United States Patent [19]

Sizto et al.

[11] Patent Number: 5,556,764

[45] Date of Patent: Sep. 17, 1996

[54] METHOD AND APPARATUS FOR CELL COUNTING AND CELL CLASSIFICATION

[75] Inventors: Ning L. Sizto, Freemont; Louis J. Dietz, Mountain View, both of Calif.

[73] Assignee: Biometric Imaging, Inc., Mountain View, Calif.

[21] Appl. No.: 236,645

[22] Filed: May 2, 1994

Related U.S. Application Data

[63] Continuation-in-part of Ser. No. 18,762, Feb. 17, 1993, abandoned.

[51] Int. Cl.$^6$ .................................................. G01N 33/53
[52] U.S. Cl. ................ 435/7.24; 435/288.7; 435/968; 435/973; 436/172; 436/805; 382/133; 382/134
[58] Field of Search ................................. 356/244, 246, 356/427; 382/128, 133, 134; 250/432 R, 458.1, 459.1, 461.1, 461.2; 435/7.1, 7.2, 7.21, 7.22, 7.23, 7.24, 7.25, 805, 288.7, 968, 973; 422/50, 55, 57–59, 68.1, 73, 82.05; 436/172

[56] References Cited

U.S. PATENT DOCUMENTS

| | | | |
|---|---|---|---|
| 3,900,265 | 8/1975 | Merlen et al. | 356/200 |
| 3,918,812 | 11/1975 | Holm | 356/73 |
| 3,999,047 | 12/1976 | Green | 235/151.3 |
| 4,045,772 | 8/1977 | Bouton et al. | 340/146.3 B |
| 4,060,713 | 11/1977 | Golay | 364/416 |
| 4,097,845 | 6/1978 | Bacus | 340/146.3 CA |
| 4,122,518 | 10/1978 | Castleman et al. | 364/300 |
| 4,129,854 | 12/1978 | Suzuki et al. | 340/146.3 CA |
| 4,175,859 | 11/1979 | Hashizume et al. | 356/39 |
| 4,191,940 | 3/1980 | Poleyn et al. | 382/128 |
| 4,199,748 | 4/1980 | Bacus | 340/146.3 CA |
| 4,229,797 | 10/1980 | Ledley | 364/515 |
| 4,282,412 | 8/1981 | Hansen et al. | 23/230 B |
| 4,318,886 | 3/1982 | Kawahara et al. | 422/82.05 |
| 4,513,438 | 4/1985 | Graham et al. | 382/6 |
| 4,523,278 | 6/1985 | Reinhardt et al. | 364/413 |
| 4,562,593 | 12/1985 | Ooe et al. | 382/6 |
| 4,647,531 | 3/1987 | Kamentsky | 435/7 |
| 4,665,553 | 5/1987 | Gershman et al. | 382/6 |

(List continued on next page.)

OTHER PUBLICATIONS

James H. Tucker, O. A. N. Husain, Keith Watts, Stephen Farrow, Royston Bayley and Margaret H. Stark, "Automated Densitometry of Cell Populations in a Continuous–motion Imaging Cell Scanner", pp. 3315–3324, 1987, *Applied Optics*.

Alan Landay, Betsy Ohlsson–Wilhelm and Janis V. Giorgi, "Application of Flow Cytometry to the Study of HIV Infection", pp. 479–497, 1990, *AIDS*.

(List continued on next page.)

*Primary Examiner*—James C. Housel
*Assistant Examiner*—Gary Tanigawa
*Attorney, Agent, or Firm*—Fulwider Patton Lee & Utecht, LLP

[57] ABSTRACT

A method and an apparatus for analyzing a material within a container, such as blood within a capillary in a volumetric cytometry system provides for detecting the edges of the container, counting the cells within the container, characterizing the cells within the container, and evaluating channels of data which contain information relevant to more than one of the detectable characteristics of the cells. A scanner scans a container of material including certain cells. Sampling circuitry is coupled to the scanner to generate scanned images of the material in the container. Two or more scanned images are generated based on fluorescence data from dyes that have overlapping spectra. The two scanned images are processed using a linear regression analysis among corresponding pixels in the scanned images near certain cells to characterize relative contents of two fluorescing dyes in a target cell. Target cells are identified from the scanned images using processing resources which identify a peak sample within a neighborhood, and compare the amplitude of the peak with the amplitude of pixels on the perimeter of the neighborhood. Upon identifying a target cell in this manner, data from the plurality of scanned images corresponding to the identified cell are saved for further analysis.

15 Claims, 13 Drawing Sheets

U.S. PATENT DOCUMENTS

| | | | |
|---|---|---|---|
| 4,672,559 | 5/1987 | Jansson et al. | 364/525 |
| 4,700,298 | 10/1987 | Palcic et al. | 364/414 |
| 4,727,020 | 2/1988 | Recktenwald | 435/6 |
| 4,741,043 | 4/1988 | Bacus | 382/6 |
| 4,845,552 | 7/1989 | Jaggi et al. | 358/93 |
| 5,068,909 | 11/1991 | Rutherford et al. | 382/302 |
| 5,072,382 | 12/1991 | Kamentsky | 364/413.08 |
| 5,107,422 | 4/1992 | Kamentsky et al. | 364/413.08 |
| 5,121,436 | 6/1992 | Kasdar et al. | 382/128 |

OTHER PUBLICATIONS

Green, J. E., "A Practical Application of Computer Pattern Recognition Research, The Abbott ADC–500 Differential Classifier", The Journal of Histochemistry and Cytochemistry, vol. 27, No. 1, pp. 160–173, 1979.

Megla, G. K., "The LARC Automatic White Blood Cell Analyzer", ACTA Cytologica, vol. 17, No. 1, pp. 3–14, 1973.

Lovett, E. J. et al., "Application of Flow Cytometry Diagnostic Pathology", Laboratory Investigation, vol. 50, No. 2, pp. 115–139, 1984.

Reich, S. et al., "Precision Digital Position Encoding for Resonant Scanners", SPIE vol. 498 Laser Scanning and Recording, pp. 169–174, 1984.

Reich, S., "The Use of Electro–Mechanical Mirror Scanning Devices", SPIE vol. 84 Laser Scanning Components & Techniques, pp. 47–56, 1976.

Tweed, D. G., "Resonant Scanner Linearization Techniques", SPIE vol. 498 Laser Scanning and Recording, pp. 161–168, 1984.

Burger, D. et al., "Acousto–Optic Laser–Scanning Cytometer", Cytometry vol. 9, pp. 101–110, 1988.

Kamentsky, L. A. "Cell Identification and Sorting", Chapter 4 Computers in Biochemical Research, 3, pp. 107–144, 1969.

Kamentsky, L. A., "Future Directions for Flow Cytometry", The Journal of Histochemistry and Cytochemistry, vol. 27, No. 12, pp. 1649–1651, 1979.

Evans, D. M., "Cytology Automation", Proceedings of Second Tenovus Symposium, Cardiff 24th–25th, pp. 231–242, Oct. 1968.

$Ch0 = m(Ch1) + a$

METHOD AND APPARATUS FOR CELL COUNTING AND CELL CLASSIFICATION

CONTINUING APPLICATION DATA

The present application is a continuation-in-part of Ser. No. 8/018,762 filed Feb. 17, 1993, now abandoned, entitled "Method and Apparatus for Volumetric Capillary Cytometry", assigned to the same assignee of the present application.

CROSS REFERENCE TO RELATED APPLICATION

The present application is related to U.S. patent application entitled "Method and Apparatus for Volumetric Capillary Cytometry", invented by Baer et al, Ser. No. 08/236,342, now pending, owned by the same assignee. The related application is incorporated by reference as if fully set forth herein.

BACKGROUND OF THE INVENTION

1. Field of the Invention

The present invention relates generally to the processing of volumetric capillary cytometry data for the purpose of counting and characterizing cells or cell constituents in a volume of material.

2. Description of Related Art

The optical analysis of biological specimens, such as blood, has widespread applications. There are many computer controlled instruments in the market for providing such analysis, including flow cytometers, automated blood cell analyzers and blood cell classifiers.

As described in the above cross-referenced application, a volumetric cytometry instrument has many advantages. In particular, the amount of blood being analyzed is controllable, the handling of the blood is reduced, and analyzed samples of blood can be stored for further processing.

However, the processing of blood samples in a volumetric system raises a number of problems. Particularly if counting of blood cells is required, it is necessary to analyze the entire volume in the capillary or other container which holds the material to be analyzed. Blood cells on the side of a container may be difficult to detect, if the analysis instrument is not calibrated for the precise dimensions of the container. For instance, in Kamentsky, U.S. Pat. No. 5,072,382, samples of blood were applied to a slide. A region to be analyzed was defined by synchronization pulses in the scanning apparatus. (See column 14, lines 49–63 of Kamentsky). Synchronization pulses in the scanning mechanism cannot be precisely aligned with a container such as a capillary or cuvette for a blood sample because of the variations in the shapes of such containers, and variations in the alignment of mounts for the containers in the scanning mechanism. It will be appreciated that the ability to precisely mount and manufacture containers is quite advanced. However, the scanning of containers for the purposes of processing cells may require resolution on the micron scale.

An additional difficulty arises because of the characteristics of dyes used to mark target cells. For instance, when analyzing cells for the presence of specific antibodies, it is common to tag the cells with dyes which fluoresce with a particular spectrum in response to an excitation beam. If more than one antibody is to be detected, more than one dye is used. However, the fluorescence spectrums of various dyes may overlap. Thus, it is difficult to fully process the information in detected fluorescence generated by plural dyes with overlapping spectra.

Furthermore, when it is necessary to count a particular number of target cells within a volume, to achieve a statistically valid count, a relatively large sample must be used. A large sample of blood, when it is scanned on the micron scale, can generate very large amounts of data. It is important for practical analysis machines that the data be processed in a reasonable amount of time. For instance, as described in the above cross-referenced application, the sample can scan for the presence of two dyes with overlapping spectra, with two channels of data. Each channel of data includes information relevant to both dyes. Further, the scan involves about 10,000 lines of 200 pixels each, resulting in 2 million samples per channel, which for 2 bytes per sample in 2 channels amounts to a total of 8 megabytes of raw data.

Furthermore, the fluorescence monitoring techniques are susceptible to a low signal-to-noise ratio. Thus, it is important to be able to process these large amounts of data with high background noise to accurately characterize and identify target cells within the volume, particularly when unbound antibody is present.

Accordingly, it is desirable to provide a method and apparatus for processing data from a volumetric cytometry system which is robust and accurate. Further, the system should be relatively fast and operate in a system having a relatively low memory requirement.

SUMMARY OF THE INVENTION

The present invention provides a method and an apparatus for analyzing a sample of cells or cell constituents, including but not limited to blood, within a capillary in a volumetric cytometry system. According to the invention, the sample cells or cell constituents have one or more detectable characteristics. The system provides for detecting the edges of the container, counting the cells or cell constituents within the container, characterizing the cells or cell constituents within the container, and evaluating channels of data which contain information relevant to more than one of the detectable characteristics of the cells or cell constituents.

Accordingly, the present invention can be characterized as an apparatus which comprises a scanner for scanning a container of sample including target cells or cell constituents. Data sampling circuitry is coupled to the scanner to generate scanned images of the sample in the container. According to one aspect, the scanner and data sampling circuitry produce a plurality of channels of data, and a corresponding plurality of scanned images. A processing system is coupled to the sampling circuitry, and includes resources to count and/or characterize the target cells or cell constituents in response to the scanned images.

These processing resources, according to one aspect, are capable of processing the scanned image, which includes information relevant to more than one of the detectable characteristics of the cells or cell constituents, to distinguish such detectable characteristics. Such resources may include software for performing a correlation analysis between the scanned image having information relevant to more than one characteristic and another scanned image in the plurality of scanned images. In one preferred system, two scanned images are generated based on fluorescence data from dyes that have overlapping spectra. The two scanned images are processed using a linear regression analysis among corresponding pixels in the scanned images near target cells to characterize relative contents of two fluorescing dyes in a target cell or cell constituents.

According to another aspect of the present invention, target cells or cell constituents are identified from the scanned images using processing resources which identify a peak pixel within a neighborhood, and compare the amplitude of the peak with the amplitude of pixels on the perimeter of the neighborhood. If the peak pixel value exceeds the perimeter pixel values by more than a predetermined threshold, then the resources characterize the neighborhood as containing a target cell. Upon identifying a target cell in this manner, segments of data from the plurality of scanned images corresponding to the identified cell can be saved for further analysis, such as the linear regression analysis discussed above.

Further, according to another aspect of the present invention, in addition to determining a relative contribution from more than one dye in a scanned image, a parameter indicating the intensity of the fluorescence of a target cell or cell constituents is determined by filtering the identified segments of data from the plurality of scanned images based upon the expected characteristics of target cells or cell constituents. For example, in one novel species of the invention, the segments are filtered by defining a neighborhood of pixels for each identified segment in the scanned images, wherein the neighborhood is larger than the expected size of the target cell. The pixels within the neighborhood are processed to compensate for background noise and generate an intensity value for the target cell within the neighborhood, based solely on pixel values within the neighborhood. For instance, this processing may involve a matched filter multiplying the intensity values of the neighborhood of a cell by a set of values which reflects the expected intensity profile of a typical cell. The resulting products are summed to yield an amplitude estimate which optimizes signal to noise ratio for that cell. The perimeter of the neighborhood is determined based on the expected shape of the target cells or cell constituents within the neighborhood.

According to yet another aspect of the present invention, the processing resources perform edge detection, and ignore contributions to the scanned images which fall outside of the detected edges of the container.

In the preferred system, the cells or cell constituents are characterized using a slope value determined from the linear regression analysis over a neighborhood defined for a target cell between two scanned images of the cell generated from overlapping fluorescence spectra of two dyes. Using the linear regression analysis, a "slope value" is determined for each target cell. This slope value is then multiplied by the intensity value of the neighborhood in one of the scanned images to produce an analysis coordinate. The cell or cell constituents is characterized based upon the position of the analysis coordinate on a characterization graph. The characterization graph is defined with a first region within which target cells or cell constituents having one dye should fall, a second region within which target cells or cell constituents having the second dye should fall, and a third region within which target cells or cell constituents stained with both dyes should fall. The regions are defined based on the background signal characteristics of the scanned images for the purposes of signal immunity and more accurate characterizations.

The present invention can also be characterized as a method for analyzing the sample within such a container. The method includes the following:

scanning the material with a detector to generate a plurality of channels of data, in which at least one of the channels may contain information relevant to more than one of a plurality of detectable characteristics of the target cells or cell constituents;

sampling the plurality of channels of data to produce a plurality of scanned images of the sample; and analyzing the plurality of scanned images to characterize the target cells or cell constituents in response to the plurality of channels of data, including processing the scanned image corresponding to the one channel which includes information relevant to more than one characteristic to distinguish such detectable characteristics, processing at least one of the plurality of scanned images to identify segments in the plurality of scanned images containing target cells or cell constituents, filtering identified segments of data based upon expected characteristics of target cells or cell constituents to generate respective intensity values for the identified segments, and characterizing the target cells or cell constituents based on the intensity value in at least one of the plurality of scanned images for a particular segment, and a value based on correlation analysis (such as the slope in a linear regression analysis) between two scanned images of a segment of data.

The system may also include analyzing at least one of the scanned images to detect the edges of the container, and ignoring data found outside of the detected edges. Furthermore, the process of characterizing the intensity value for a particular segment of data may include defining a neighborhood of pixels for each identified segment, the neighborhood being larger than the expected size of the target cell, and processing the pixels within the neighborhood to compensate for background signal and generate an intensity value for the target cell or cell constituents within the neighborhood.

Other aspects and advantages of the present invention can be seen upon review of the figures, the detailed description, and the claims which follow.

DETAILED DESCRIPTION

Figure 1:
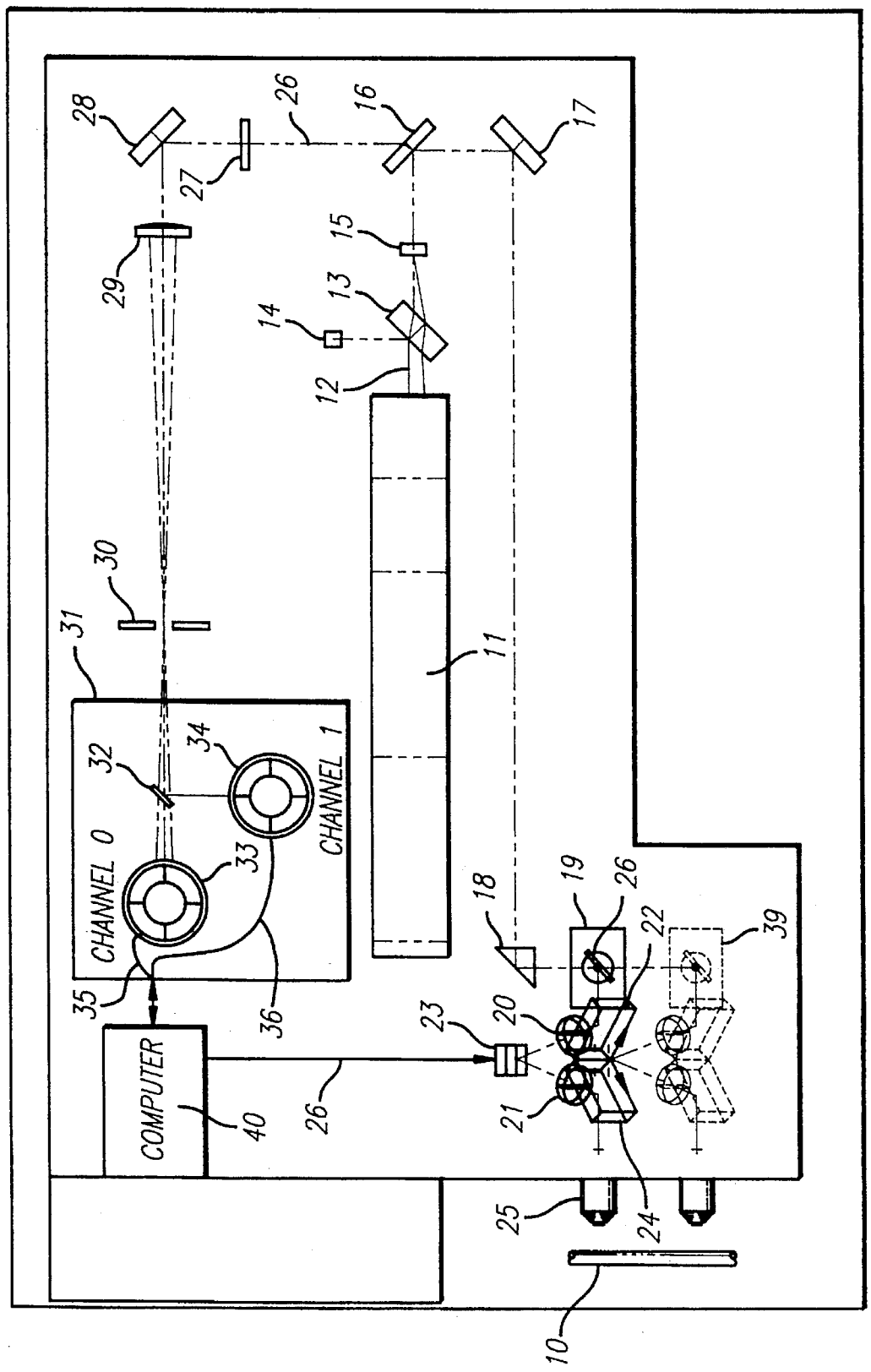
FIG. 1 is a plan view of a scanner apparatus with a data processing system according to the present invention.
Figure 2:
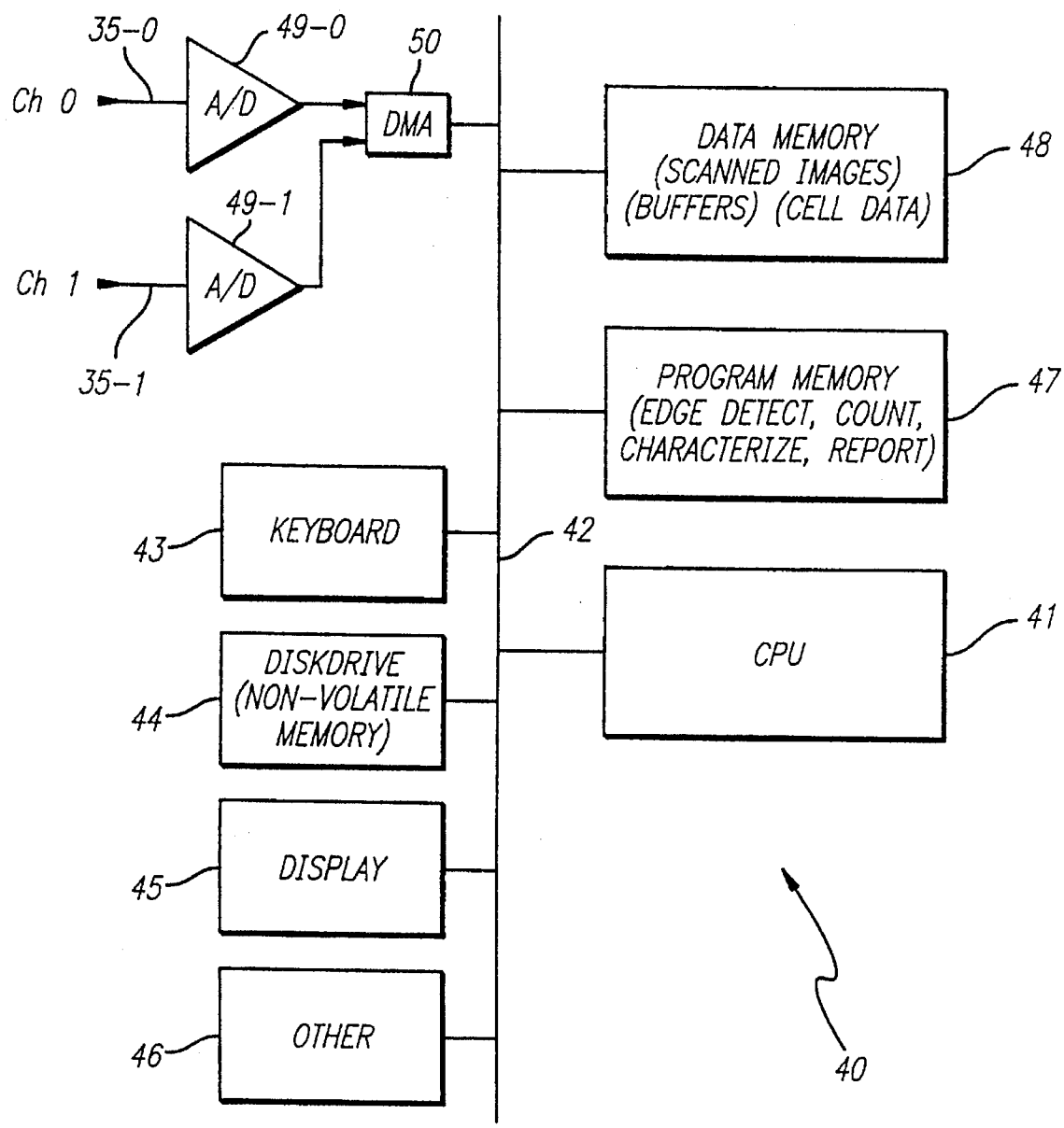
FIG. 2 is a schematic block diagram of the data processing system used in combination with the system of FIG. 1.

A detailed description of preferred embodiments of the present invention is provided with respect to the figures. FIGS. 1 and 2 illustrate a hardware environment for the present invention. FIGS. 3–13 provide an explanation of the processing resources used to count and characterize target cells or cell constituents according to the present invention.

As can be seen in FIG. 1, an apparatus for volumetric capillary cytometry is provided. The machine is designed to process material within a capillary 10, which has a known volume. In the preferred system, the capillary may be rectangular in cross-section, having a width of about 0.4 millimeters to 1.5 millimeters, a length of about 40 millimeters, and a depth of about 25 to 225 microns, and in one embodiment, 100 microns. This capillary is suitable for detecting or characterizing a variety of cells or cell constituents. In one embodiment, it is used for the characterization of a CD3/CD4 assay, in which concentration of CD3 and CD4 antibodies are to be determined. In this type of assay, there are typically three populations present: CD3 positive cells stained with a Cy5 labelled antibody only; CD4 cells stained with both a Cy5 labelled CD3 antibody and a CyFr labelled CD4 antibody. Monocytes are stained with the CyFr labelled CD4 antibody only. It is found that the cells of interest in this assay are about 10 microns in diameter and are well classified using a capillary of the dimensions outlined above. It will be appreciated that the present invention is not limited to the characterization of a CD3/CD4 assay.

According to one method useful with the invention, a biological fluid, such as whole uncoagulated blood, can be reacted with an excess amount of a binding agent that contains a fluorophore excitable at a given wavelength. The fluorescently-labeled binding agent is selected to react with binding sites present within the sample. For example, a fluorescently-labeled antibody directed to the CD4 cell surface marker present on some leukocyte blood subclasses is reacted with a sample of whole blood. The labeled binding agents and the binding sites, i.e. labeled anti-CD4 antibodies and the surfaces of CD4-bearing leukocytes in the example, form fluorescent complexes that will emit a signal when used with the apparatus of the present invention.

After the fluidic sample is reacted with the labeled binding agent, it is diluted and drawn into a capillary 10. Minimal processing of the biological fluid sample is necessary to practice the method of the present invention separation of bound and unbound binding agent is not required at any point. An optical scan is made of the sample in a volumetric manner and fluorescence emission is sequentially recorded from each illuminated columnar region.

Fluorescence emission occurs from both the binding agent-binding site complexes and from the free binding agent but a more intense signal relative to background level comes from areas where the binding agent is clustered, i.e. cells or cell constituents exhibiting binding sites to which the binding agent is directed. Therefore, a signal of heightened fluorescence corresponds to a cell or cell constituents, and is recorded as such. When the fluorophores with which the anti-CD4 antibodies are labeled and excited in the given example, the fluorescence emitted and recorded as an event signifies the presence of a leukocyte that expresses the CD4 antigen.

The enumeration may occur in an absolute volume, depending on a desired application, by noting the beginning and ending points of the lengthwise scan of the capillary tube and measuring incremental steps therebetween. This quantitation of all of the fluorescent targets in a fixed, precise volume is a powerful method of quickly obtaining detailed population data.

Fluorophores that activate at different wavelengths can be combined with binding agents directed to different binding sites, so that the presence of multiple reaction moieties in the sample can be detected. From the precise known volume of the capillary tube that has been scanned, a quick reading will identify the number of cells or cell constituents of a particular subclass per unit volume that are present in the sample. To illustrate, this method can quickly distinguish and enumerate the monocyte granulocyte or lymphocyte subsets of a given volume of a blood sample through reaction of the whole sample with differentially-excitable fluorescently-labeled antibodies bound by the cell surface antigens. The T-cell leukocytes can be directed to CD3, CD4, and CD8 antigens. The optical system is simply set to excite each fluorophore at its crucial wavelength and a detection channel is created to correspond to the emission wavelength of each fluorophore. Alternatively, a ratio can be obtained without counting a precise volume, e.g. this is a rapid technique for obtaining CD4/CD8 T-cell ratios, important in determining the progression of AIDS.

When an assay is performed to determine leukocyte subclasses in whole uncoagulated blood using the technique of the present invention, a two or three minute wait between placement of the reacted sample into the capillary tube and the optical scan allows for the natural density of the numerous red blood cells present in the sample to cause settling of the red blood cells to the bottom of the capillary tube and the subsequent displacement of the white blood cells. This natural buoyant effect causes a resultant location of the white blood cells near the upper portion of the capillary tube and assists in fluorescence detection because of the top-down scan geometry of the present invention. Because of this effect, coincidence of targets is also negligible.

The scanner is based on use of a laser 11, such as a helium-neon laser (as shown), an ion laser, a semiconductor laser, or the like, which generates a laser beam along path 12. Laser 11 preferably emits in the 600 to 1000 nm range. The laser beam along path 12 passes through a beam splitter 13, such that a portion of the beam is diverted to a power meter 14 for monitoring the laser output power. The main beam passes through the beam splitter 13 to a narrow line filter 15, which selects the wavelength of interest generated by the laser 11. Next, a dichroic beam splitter 16 receives the beam which passes through the filter 15. The dichroic beam splitter diverts the selected output from the laser toward a steering mirror 17. The steering mirror 17 diverts the beam to a folding mirror or prism 18. From the folding mirror or prism 18, the beam is directed to a scanner 19.

The scanner 19 allows transverse and longitudinal scanning of the laser beam across the sample capillary 10. The scanner assembly includes a galvanometer mounted mirror 25 which rotates a few degrees back and forth in a rapid fashion at about 20–200 Hz (peak-to-peak 6°–12°). The beam is deflected by the galvanometer mounted mirror 25 to a first lens 22, through a second lens 23 and through an objective lens 24 to the capillary 10. Two lenses 22 and 23 are designed to be confocal, that is, they are separated along the optical path by their focal length, and they have equal focal lengths. It is not necessary that the lenses be confocal, but they must have overlapping focal planes. Similarly, the distance between lens 23 and the objective lens 25 of the microscope must be precisely controlled so that the beam, as it is rotated by the galvanometer mounted mirror 25, appears to be rotating about a virtual point directly in front of the microscope objective.

As schematically illustrated by ghosted outline 39, the scanning assembly 19 is designed to move longitudinally along the capillary 10 for a distance of about 40 millimeters.

A variety of other scanner mechanisms can be used as suits a particular application of the invention.

The whole scanner assembly 19 is controlled by computer 40.

The beam impinging upon the outer wall of capillary 10 traverses the wall and illuminates a columnar region of the sample causing fluorescent emission from the sample. Light collection occurs in an epiillumination manner. The emitted fluorescence is collected by microscope objective 24 and directed back, as a retrobeam. Microscope objective 24 has a central portion for passage of incident beam and uniform depth of focus of the incident beam through capillary 10. Because fluorescent emission is over a very wide angle, fluorescent collection occurs over a wider portion of microscope objective 24.

Fluorescence given off by the dyes in response to the excitation beam generated by the laser 11 retraces the optical path through the scanning mechanism 19, the prism 18, the steering mirror 17, to the dichroic beam splitter 16. The fluorescence comes from the focal point of the microscope objective 24 and is collimated with a diameter of about 8 millimeters as it comes out of the microscope objective. The dichroic beam splitter 16 allows the fluorescing wavelengths to proceed along path 26.

The beam on path 26 enters a bandpass filter 27, or a series of the same, which are designed to filter the back-scattering of the laser beam itself which are due to weak reflections from the optical elements and surfaces of the capillary. These reflections may be much stronger than the actual fluorescence that is detected from the sample.

From the bandpass filters 27, a folding mirror 28 directs the beam through a focusing lens 29. The focusing lens brings the collimated light from the sample into a focus, and through a pinhole filter 30. The light from the capillary, which arises outside the focal point of the microscope objective 25 will not be collimated when it enters the lens 29. Thus, the pinhole filter 30 rejects fluorescence from regions that are not of interest. The pinhole size is chosen so as to define a volume from which to collect fluorescence intensity from the sample. Typically, this volume is selected to be about five or ten times the expected volume of the target cells.

Through the pinhole 30, the beam enters a photomultiplier box 31. The photomultiplier box includes a dichroic beam splitter 32 which separates the detected fluorescence into two basic components. The first component, channel 0 is light having wavelengths below about 680 nanometers in the present embodiment. The second component, channel 1, is light having wavelengths above about 680 nanometers. Channel 0 is directed to a first photomultiplier 33. Channel 1 is directed to a second photomultiplier 34. First and second photomultipliers are respectively connected across lines 35 and 36 to the computer 40.

Also included in the mechanism, but not shown, is an autofocus mechanism. The autofocusing system uses an algorithm which involves measuring the fluorescence in a preliminary scan. At a first position in the capillary, the microscope objective focus is scanned to find the position of maximum fluorescence. This value is stored, and the objective is moved to a second position in the capillary. Again, focus in this position is scanned for maximum fluorescence. That value is stored. Using the two values, as a beginning and end point for the scan, the microscope focus is linearly interpolated between the two to optimize the fluorescence reading along the length. In addition, the length of each scan line is set to be slightly larger than the width of the interior of the capillary. This is done to insure that every cell is detected by overscanning capillary dimensions, and later detecting the edges of the capillary to filter irrelevant information.

FIG. 2 schematically illustrates processing resources in the computer 40. The computer 40 includes a CPU 41 coupled through a system bus 42, as schematically illustrated. On the system bus 42 are a keyboard 43, a disk drive 44, or other non-volatile memory system, a display 45, and other peripherals 46, as known in the art. Also coupled to the bus 42 are a program memory 47 and a data memory 48. The output of the photomultipliers, channel 0 and channel 1, are supplied on lines 35-0 and 35-1, respectively, through analog to digital converters 49-0 and 49-1. The outputs of the analog to digital converters are 16 bit pixel values of the analog signals from channels 0 and 1. These values are supplied through a direct memory access (DMA) circuit 50 which transfers the pixel values into the data memory 48.

The processing system 40 includes resources that store scanned images of the data for channel 0 and 1, buffers used during the processing of the data, and memory for storing cell data once the cells or cell constituents are located, characterized and/or classified. Similarly, the program memory 47 includes resources for detecting the edges of the capillary, counting and locating target cells or cell constituents within the scanned images, characterizing the target cells or cell constituents, and reporting results. More details concerning the processing resources in the computer 40 are provided below with respect to the flow charts and graphs of FIGS. 3–13. As will be appreciated, processing resources may be implemented with hardware, software, or a combination of both, as suits a particular use of the invention.

Figure 3:
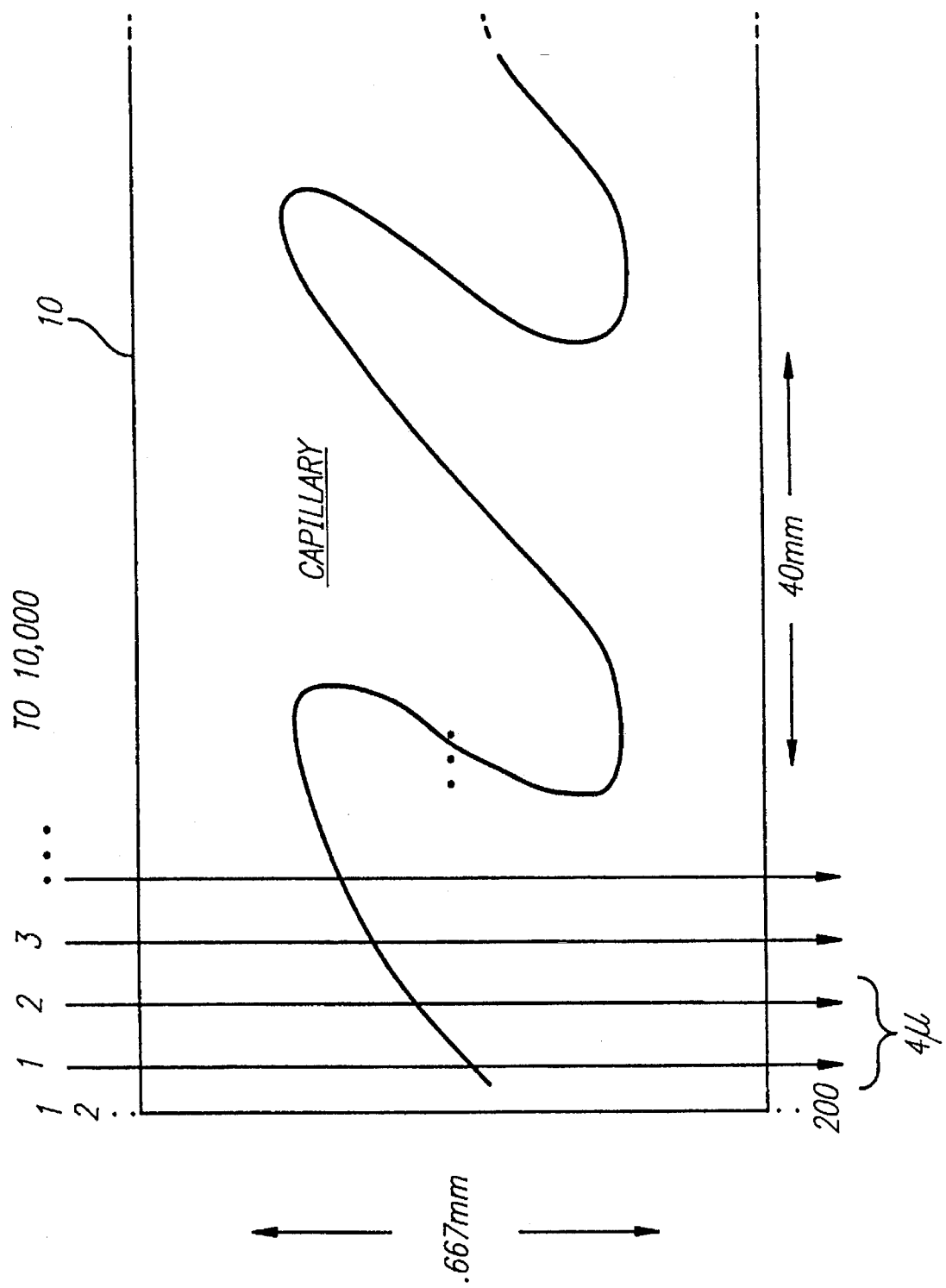
FIG. 3 is a schematic diagram illustrating the scanning process used in the scanner of FIG. 1.

FIG. 3 illustrates the scanning technique used for gathering data from the capillary. The capillary 10, as illustrated in FIG. 3, has a width of about 0.667 millimeters, and a length of about 40 millimeters. A galvanometer scanning system scans the laser beam along a track 1 on a line longer than the capillary 10 is wide. At the end of line 1, the beam snaps back to the beginning of line 2 and scans line 2. The distance between the center of lines 1 and 2 is about 4 microns in the present embodiment.

For a capillary of about 0.667 millimeters in width, the scan lines are about 0.8 millimeters long. This provides 200 four micron samples along each scan line. For a 40 millimeter long capillary, with scan lines separated by 4 microns, about 10,000 scan lines are collected for each blood sample.

Figure 4:
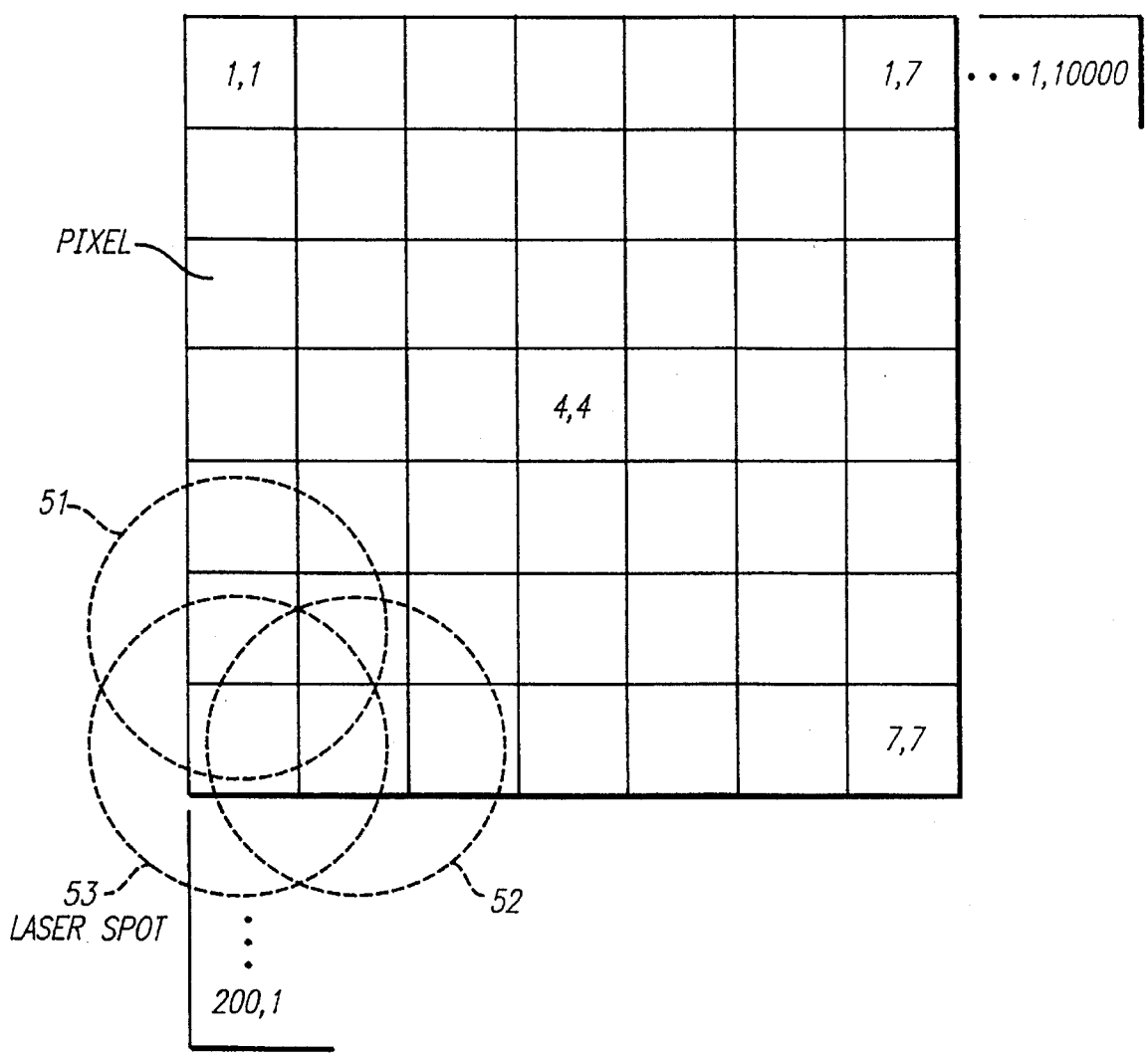
FIG. 4 schematically illustrates an organization of data in the scanned images generated by sampling the output of the scanner of FIG. 1.

The analog to digital converters sample the scanned data at a rate which creates a pixel value representing fluorescence in a spot having dimensions of about 4 microns by 4 microns. FIG. 4 illustrates a 7×7 neighborhood of pixels. Thus, in the upper left hand corner, pixel in row 1, column 1, is found. In the upper right hand corner, pixel in row 1, column 7, is found. In the center of the neighborhood of pixels, pixel row 4, column 4, is found. Similarly, in the lower right hand corner, pixel in row 7, column 7, is found.

FIG. 4 also illustrates the size of the laser spot relative to the sample dimensions. In the preferred embodiment, the laser spot 53 has a diameter of about 10 microns. Thus, oversampling occurs. That is, the laser spot 53 excites a region of 10 microns in diameter for the pixel at row 7, column 1. At row 6, column 1, a second spot 51 illuminates a region 10 microns in diameter which substantially overlaps with the spot 53 for row 7, column 1. Similarly, the spot 52 for row 7, column 2, substantially overlaps with the spot 53 and the spot 51 in column 1.

Figure 5:
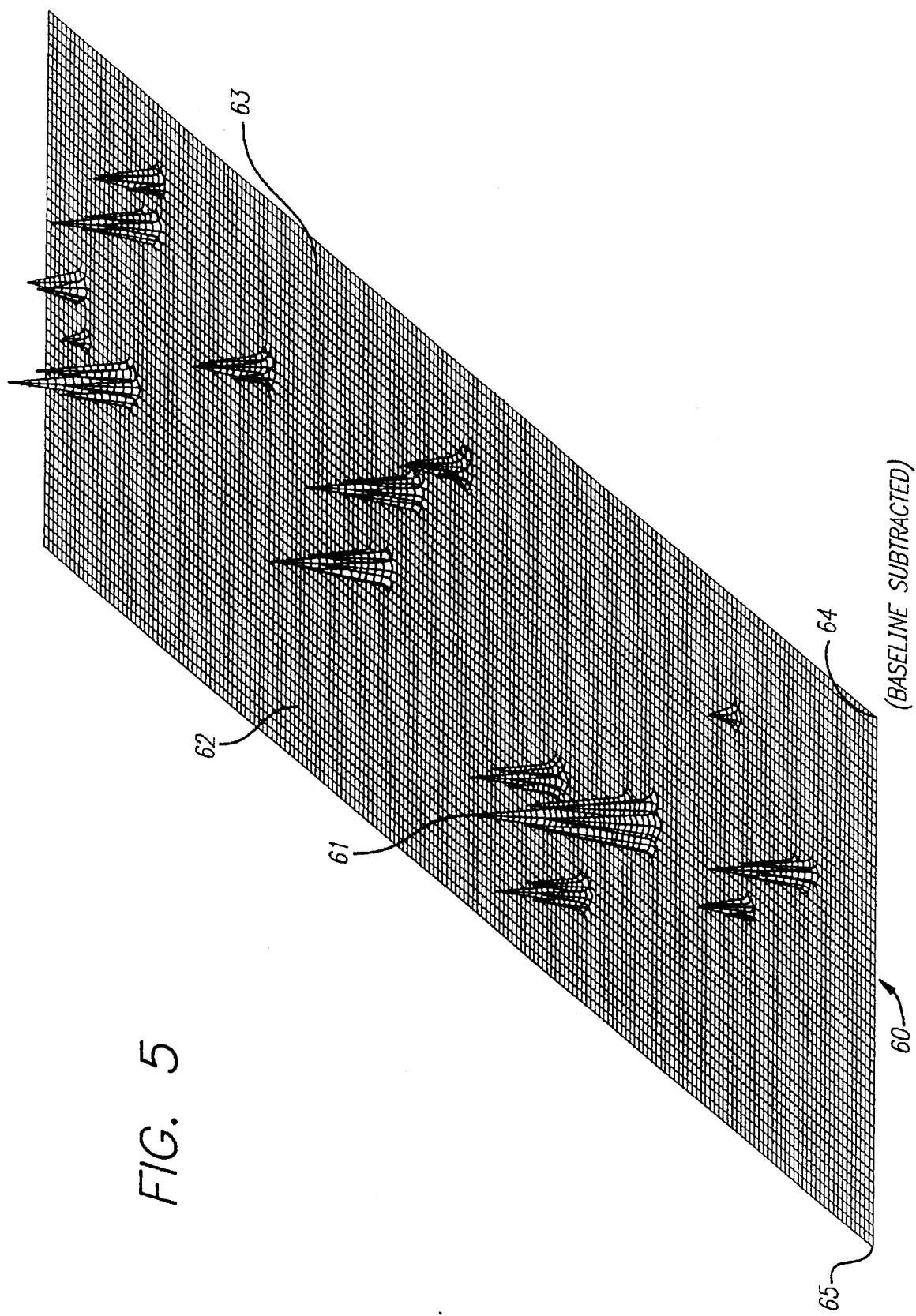
FIG. 5 is a plot of a representative scanned image from the system according to FIG. 1.

FIG. 5 illustrates a portion of a scanned image generated with one of the channels of the present invention. The graph of FIG. 5 is a baseline subtracted representation, where the baseline is illustrated at line 60. The baseline is essentially the average height of all the lines in the scan region. With this value subtracted, a number of peaks, e.g., peak 61, can be seen in the scanned image. These peaks typically correspond to target cells and are processed as described below. Also, each scan includes a region, generally 62, and a region, generally 63, which lie outside the capillary. The baseline 60 can be used to define the edges of the capillary because of the rapid falloff at 64 and 65 corresponding with the edges of the capillary. The processing resources characterizing the cells ignore pixel values outside the detected edges.

As mentioned above, there are two channels detected according to the present invention. FIG. 5 illustrates a single channel. There will be a corresponding scanned image from the second channel having a similar profile, however, the amplitudes of the peaks will differ depending on the magnitude of the fluorescence detected in the second channel. Also, some peaks may be found in one image but not the other.

Figure 6A:
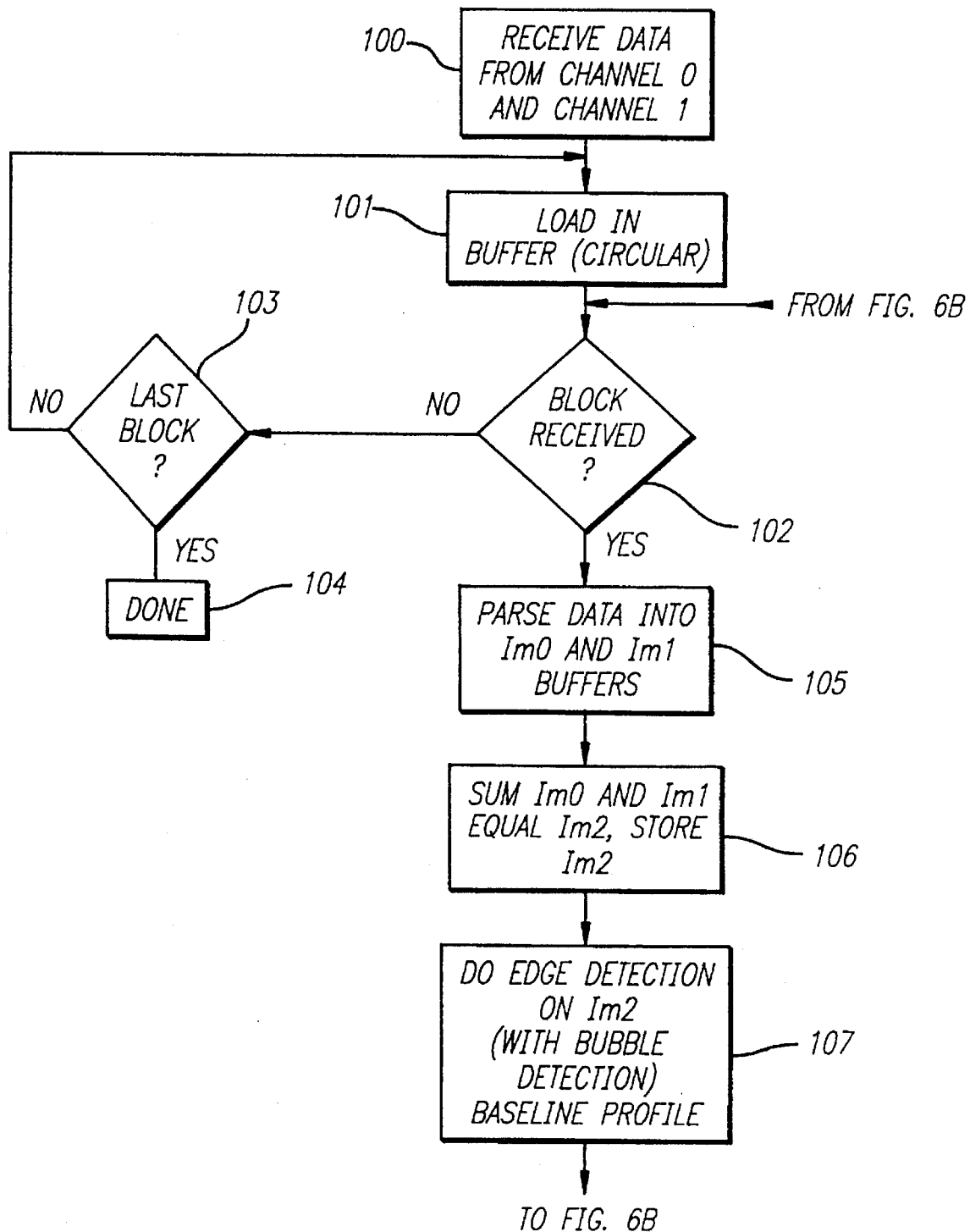
FIGS. 6A and 6B together make up a flow chart for the basic data processing loop for the system according to the present invention.
Figure 6B:
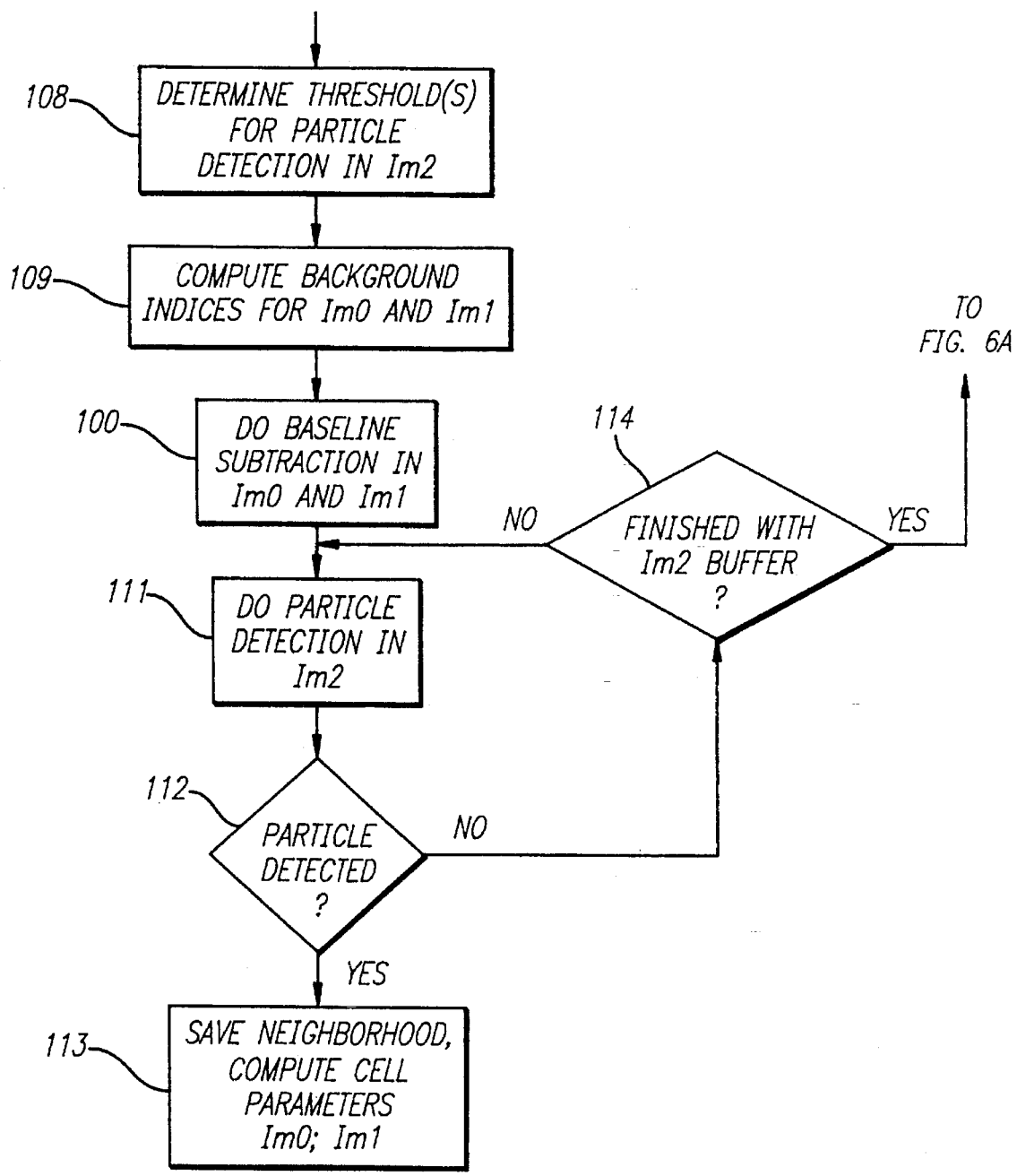

The basic data processing steps executed by the processing resources are illustrated in FIGS. 6A and 6B. The first step in FIG. 6A is to receive the data from channel 0 and channel 1 (block 100). As the data is received, the DMA circuitry loads it into a buffer in the data memory (block 101). The buffer may be a circular buffer or other data structure used to keep track of the amount of data being received. The algorithm then determines whether a block of data having a prespecified size has been received (block 102). For the purposes of the present example, about 100 to 150 scan lines may comprise a suitable block size. If a block has not yet been completely received, then the algorithm determines whether the last block from a blood sample has been received (block 103). If it has, then the algorithm is done (block 104). If it has not, the algorithm loops into block 101 to continue loading data in the buffer.

When it is detected that a complete block has been received at block 102, then the algorithm parses the data into a plurality of scanned images by dividing the data into a raster image file Im0 for the first channel, and a raster image file Im1 for the second channel (block 105).

Data pre-processing involves reading in and processing the data in blocks. The signal processing requires signed numbers, thus, the unsigned 16 bit data is converted into 15 bit signed data.

Next, the two scanned images Im0 and Im1 are summed, or averaged, to generate a composite image Im2, and the composite image Im2 is stored (block 106).

Figure 11:
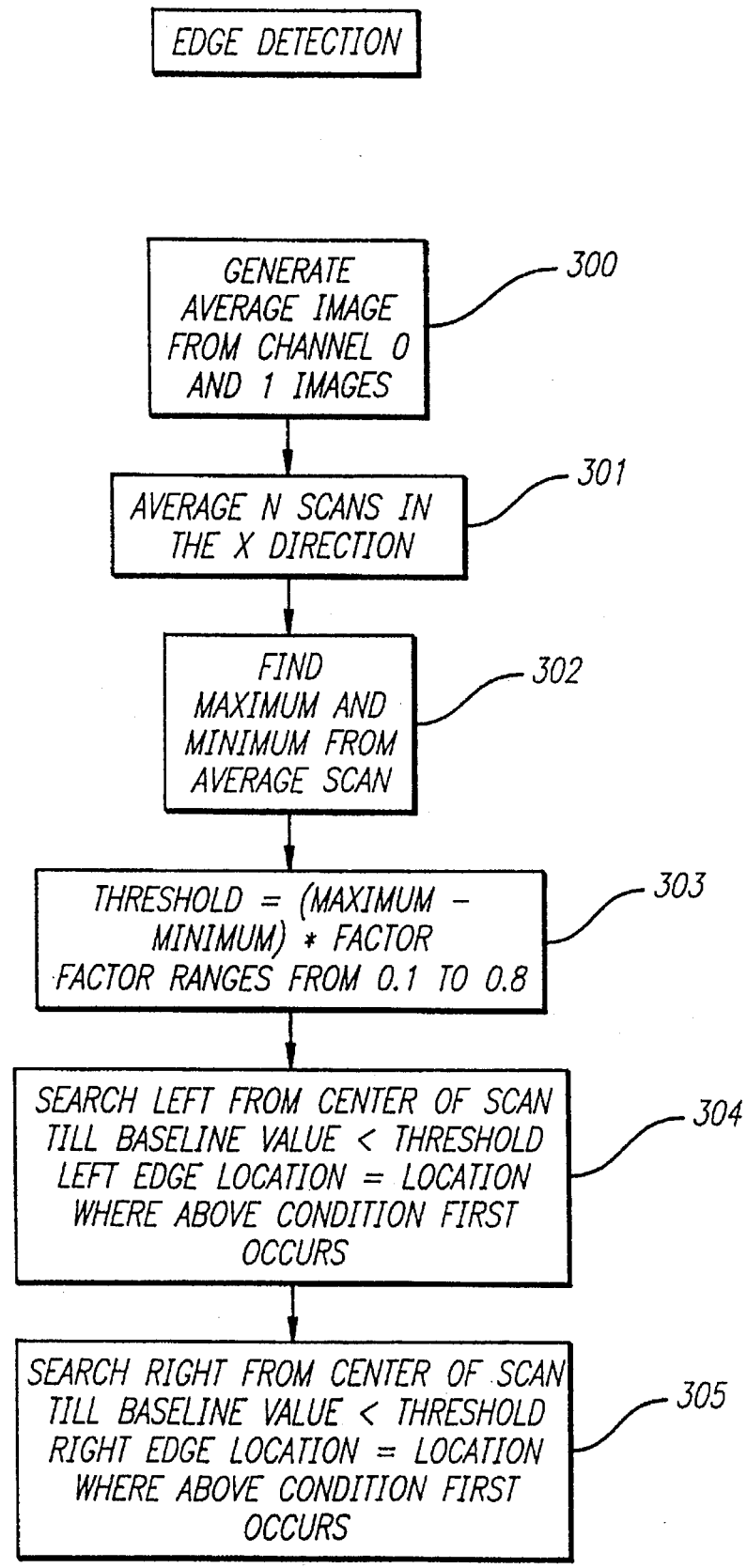
FIG. 11 is a flow chart illustrating the edge detection process according to the present invention.

Next, an edge detection algorithm, such as described below with respect to FIG. 11, is executed (block 107). The edge detection algorithm may be supplemented with an algorithm for evaluating the results to ensure that no false edges, such as might be detected by a bubble in a capillary, are found.

The edge detection is done using a baseline profile, where the baseline is the average of all the scans in the block, ignoring the scans that have peaks higher than a certain threshold.

After block 107, the algorithm proceeds to determine thresholds to be used for particle detection in the composite image Im2. These thresholds may be prespecified, empirically determined values, or they may be adaptively computed for each buffer or each sample. One algorithm for determining the threshold may involve determining the maximum and minimum values for each 7×7 pixel neighborhood in the block being processed. The maximum minus minimum value with the highest frequency of occurrence is used to estimate the threshold for particle detection. Distribution of the maximum and minimum for peaks of neighborhoods in the buffer are determined, and the thresholds are set so that peaks are detected if the maximum and minimum values in the neighborhood differ by amounts smaller than a threshold 3 standard deviations below the average peak height.

Figure 10:
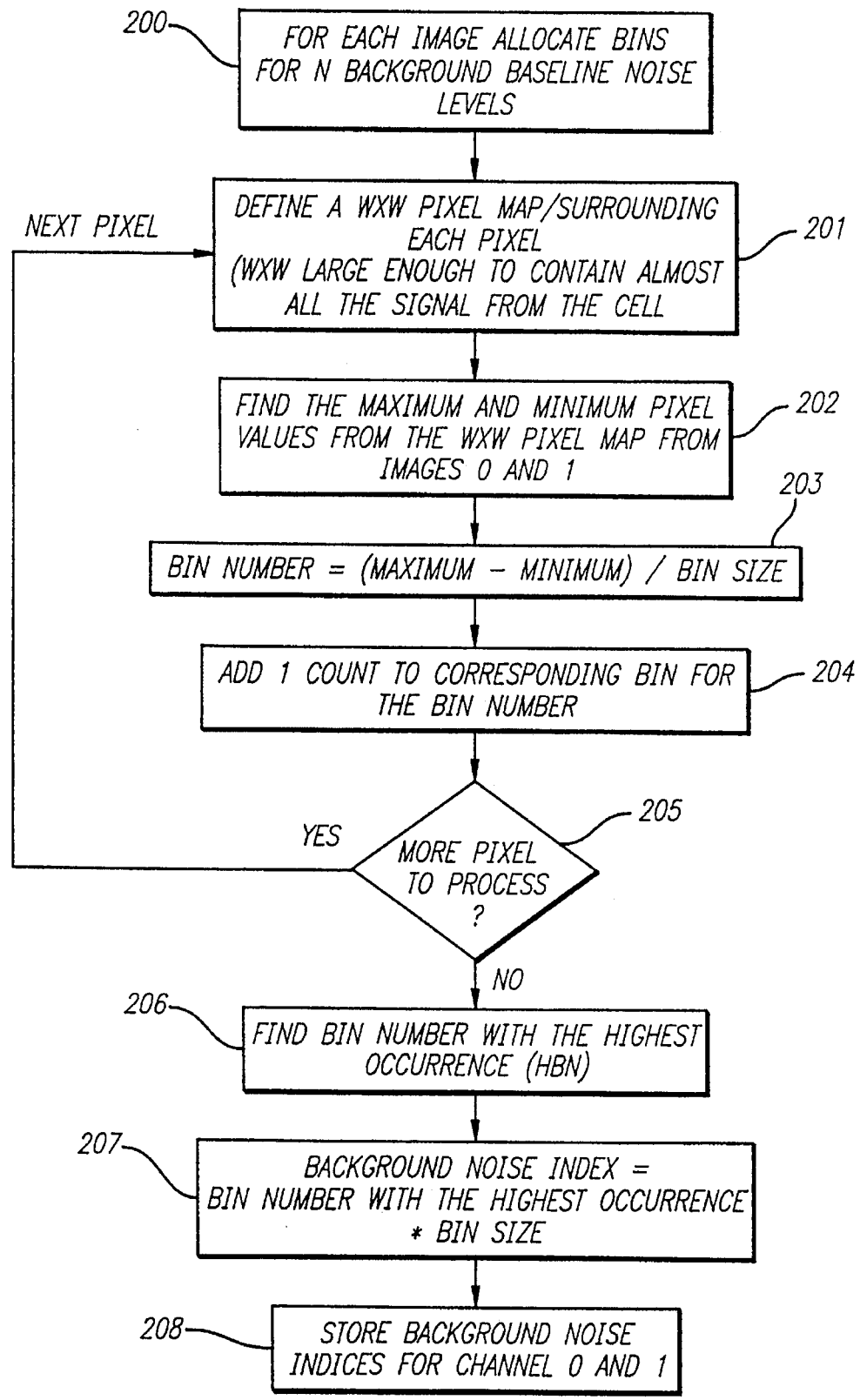
FIG. 10 is a flow chart illustrating the generation of background noise indices according to the present invention.

After determining the thresholds for particle detection in block 108, the algorithm proceeds to compute the background indices for the scanned images Im0 and Im1 using an algorithm such as described with respect to FIG. 10 (block 109). After computing the background indices, the algorithm may then proceed to do a baseline substraction step for the scanned images Im0 and Im1 (block 110). This is an optional step, depending on the techniques used for particle detection and cell characterization set out below.

One baseline removal technique involves finding the minimum, or average of the N minimum lowest points along a given scan (N equal about 10). The above minimum, or average minimum, is then subtracted from all pixels in the block, and negative values are clipped to 0. Baseline removal is optional. In particular, if cell detection uses the peak slope criteria, as described below, it is not necessary to do baseline removal. However, it may be desirable to have baseline subtraction to eliminate edge effects in an overscanning situation.

After baseline subtraction for images Im0 and Im1, the algorithm does a particle detection routine using image Im2 (block 111). The particle detection process is illustrated below with respect to FIG. 12.

The next block determines whether a particle is detected (block 112). If a particle is detected, then the neighborhoods of pixels from images Im0, Im1 and optionally Im2 are saved (block 113), and cell parameters are computed using data in the neighborhood of the pixel maps, e.g. in response to the saved neighborhoods. If a particle is not detected, then the algorithm determines whether the Im2 buffer has been completely processed for particle detection (block 114). If not, the algorithm loops to block 111 to continue the particle detection routine. If the buffer has been finished, then the algorithm loops to block 102 in FIG. 6A, as illustrated, to begin processing a next block of data.

Thus, for example, the raw data consists of two 200×N (where N is less than or equal to 10,000) raster image files for each channel 0 and channel 1, where each pixel is a 16 bit unsigned integer, generated by the output of the analog to digital converters. The image data may be processed in blocks. Data for scan lines at the boundaries of the image block may be buffered to deal with cells crossing the image block boundaries.

The data block size is 200 pixels high by N scans wide, where N is about 128. The buffered block size may be 200×16 pixels on the block boundaries. By image processing in blocks, a smaller amount of memory resources are used for the image processing.

The technique of saving the neighborhood values from the scanned images for each block, as particles are detected, and then continuing to process additional blocks allows real time gathering of data and cell or cell constituent detection, with ability to compute cell parameters and characterize the cell later, or with a time shared processing technique. This greatly enhances the efficiency of use of the computation resources to allow sampling of very large amounts of scanned data in substantially real time.

Cell and cell constituent characterization, according to a preferred embodiment of the present invention, involves utilizing information from the two channels. The two channels in the present system include data which is relevant to both of the dyes which are to be detected. Thus, a technique must be used to discriminate information from the two dyes in the two channels that is efficient and noise immune. Accordingly, one species of the present invention applies a linear regression technique over the neighborhoods of pixels saved for detected particles.

Figure 7:
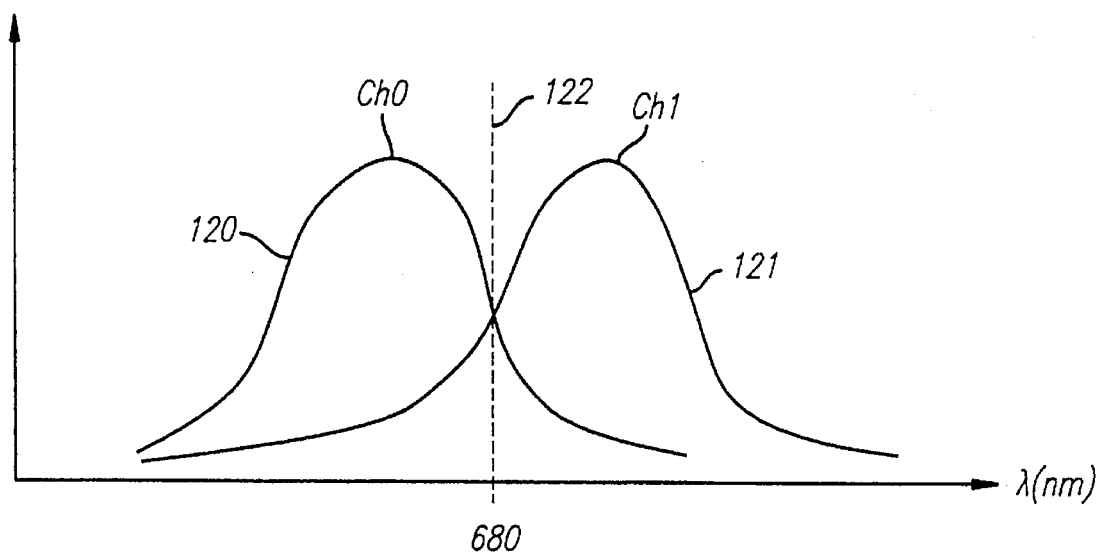
FIG. 7 illustrates the overlapping spectra of two dyes which are analyzed according to the present invention.

The problem to be solved can be appreciated with respect to FIG. 7, which schematically illustrates the spectra of fluorescence for the two dyes detected by channel 0 and channel 1, respectively. Thus, a cell containing antigens stained by the first dye will fluoresce with a spectrum such as spectrum 120. Similarly, the cell with a dye attached to an antigen of the second type will fluoresce with the spectrum 121. As can be seen, the two spectra substantially overlap. The dichroic beam splitter 32 in the photomultiplier mechanism 31, as shown in FIG. 1, splits the fluorescent beam along the 680 nanometer line 122 to generate two signals. This line has been empirically determined for the presently described system to provide good separation. Thus, the two signals both contain information which is generated in response to both dyes.

Figure 8:
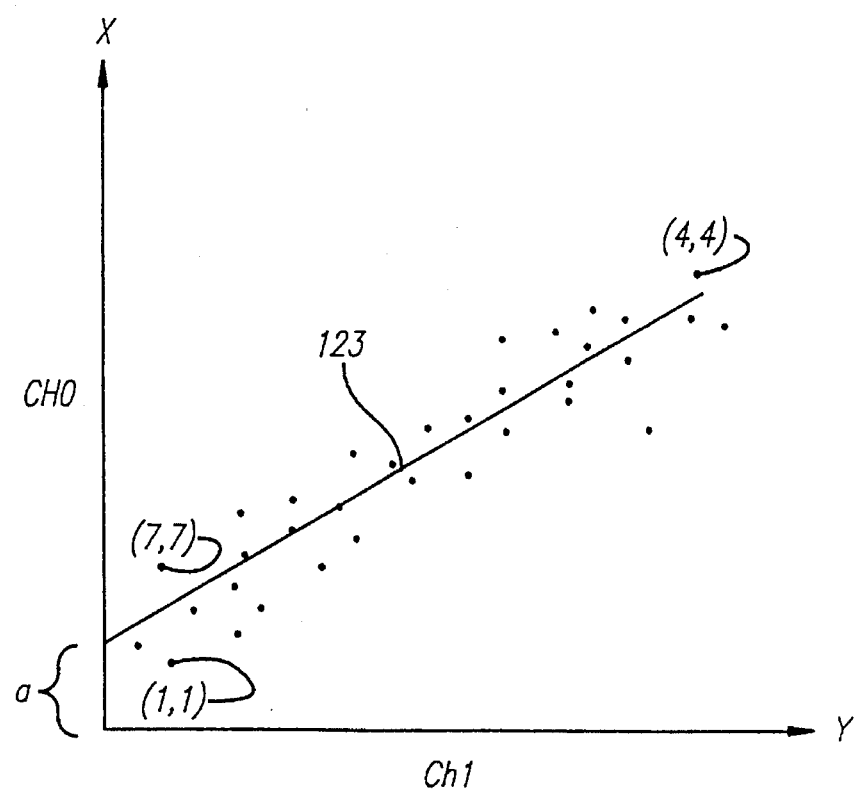
FIG. 8 is a graph illustrating the linear regression analysis used in the characterization of cells according to the present invention.

The linear regression technique utilized to discriminate the information in the two channels is described with reference to FIG. 8. In particular, a 7×7 neighborhood of pixels is saved from each of image Im0 and Im1, centered on each target cell which is detected using the algorithm of FIGS. 6A and 6B. The 49 coordinates may be plotted as shown in FIG. 8, where each dot is positioned with the magnitude of the first channel on axis X and the magnitude of the second channel along axis Y, such that sample at row 1, column 1, and sample at row 7, column 7, may appear at the points (1, 1) and (7, 7). Similarly, the sample at row 4, column 4, may appear at the point (4, 4). As can be seen, the sample from row 4, column 4, will have the highest average of amplitude from both channels because of the cell classification technique. The dots are then applied to a linear regression algorithm, as well known in the art, to find the best fit line 123 to the dot plot, Pres et al., *Numerical Recipes in C*, 1988, p. 523. This produces the slope "m" and the offset "a" for each target cell. Thus, the magnitude of the contribution from channel 0 can be expressed as the slope "m" times the magnitude of the contribution of channel 1, plus the offset value "a".

Figure 9:
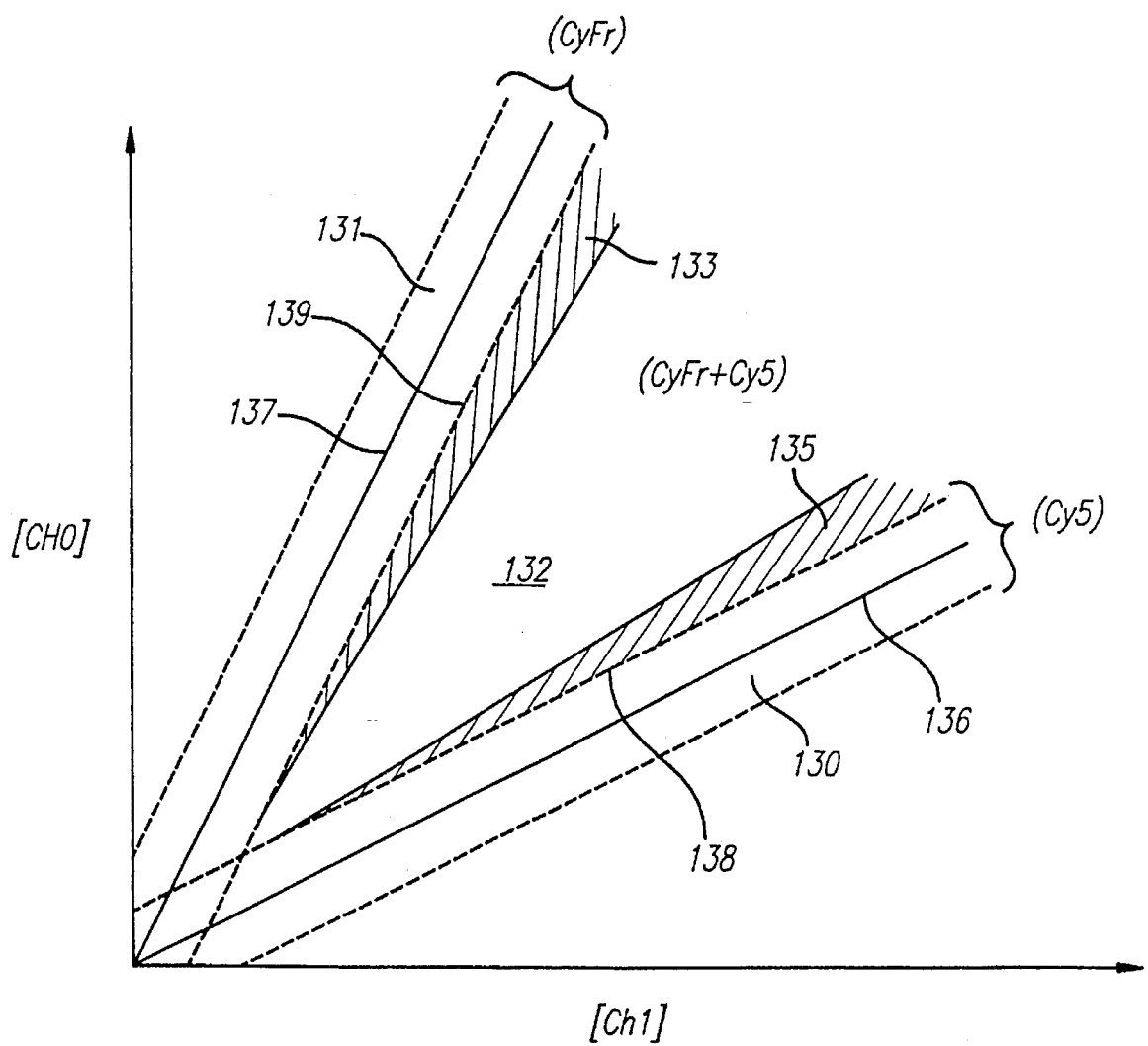
FIG. 9 illustrates a cell classification graph used for classifying cells based on channels of data which include overlapping information, according to the present invention.

FIG. 9 is a graph which illustrates the technique used for characterizing the detected cells. In particular, the intensity value for a detected cell is defined as [CH1] for the scanned image Im1 and [Ch0] for the scanned image Im0 in the respective 7×7 neighborhoods. This intensity value is determined by a matched filtering technique based on expected characteristics of target cells over the 7×7 neighborhoods.

A matched filter can be constructed from expected or typical pixel values in the neighborhood of a cell. The matched filter is a matrix of coefficients which will be multiplied with the corresponding pixels from the neighborhood of the detected cell. The 49 resulting products can be summed to yield a single intensity value ([CH0] or [CH1]) for the detected cell. The coefficients can be chosen to sum to zero, in which case the constant background signal is cancelled out.

The intensity value for the cell is then plotted on the graph of FIG. 9 by multiplying the slope determined using the linear regression analysis above by the intensity value of one of the channels.

As can be seen, the graph of FIG. 9 is divided into five regions. The first region, 130, is for target cells which are dyed substantially only with the first dye which is centered on channel 1. The second region, 131, is defined for target cells which are dyed substantially only with the second dye. The third region 132 is defined for cells which are believed to be stained with both dyes. The fourth region 133 and the fifth region 135 are a "no call" region to ensure that bad data is ignored.

The first region 130 is defined during calibration of the device by doing a scan of a sample dyed only with the first dye. Linear regression analysis is applied to create a line 136 based on the one dye detection from channel 1. A similar technique is used to define line 137 for the second dye which has most of its spectrum detected by channel 0. A background index is calculated for the buffer in question to define regions indicated by dotted lines 138 and 139 below which for channel 1 and above which for channel 0, samples are characterized as having only one dye. The samples which fall in the region 132 are characterized as having both. Samples which fall in the regions 133 and 135, or which have a magnitude value which is too low, are characterized as no calls.

Appendix A provides a source code for the cell characterization routine according to one embodiment of the present invention as a means of providing an example of processing resources which might be used to accomplish this sort of classification.

The goal of cell or cell constituent classification is to determine the decision boundaries based on population-independent parameters. If necessary, the boundaries determined can be validated with population statistics.

In the CD3/CD4 assay, there are 3 cell populations present. The CD3 positive cells are stained with the Cy5 labeled antibody only. The CD4 cells are stained with both the Cy5 labeled CD3 antibody and the CyFr labeled CD4 antibody. The monocytes are stained with the CyFr labeled CD4 antibody only.

Since the CD3 positive cells and the monocytes are stained with one dye only, their slope distributions should cluster around the Cy5 and CyFr slopes respectively. The Cy5 and CyFr slopes are determined in the compensation matrix calibration. The spread or distribution of the clusters can be determined from the background noise estimates.

Similarly, in the CD3/CD8 assay, there are 3 cell populations present. The CD3 positive cells are stained with the Cy5 labeled antibody only. The CD8 cells are stained with both the Cy5 labeled CD3 antibody and the CyFr labeled CD8 antibody. The NK cells are stained with the CyFr labeled CD8 antibody only.

Since the CD3 positive cells and the NK cells are stained with one dye only, their slope distributions should cluster around the Cy5 and CyFr slopes respectively. The Cy5 and CyFr slopes are determined in the compensation matrix calibration. The spread or distribution of the clusters can be determined from the background noise estimates.

The following classification rules may be applied:
Non-Cells
A particle is classified as non-cell, if any of the following criteria is met:
1. Particles with correlation coefficient (for the regression fit for planes 0 and 1) less than the threshold value (0.8).
2. Channel 0 value less than background noise threshold.
3. Channel 1 value less than background noise threshold.
Monocytes and NK Cells
1. Cells with channel 1 value greater than the CyFr slope line minus a constant background noise offset for channel 1.
CD3 Cells
1. Cells with channel 1 value less than the Cy5 slope line plus a constant background noise offset for channel 1.
CD4/8 Cells
Any cell that does not satisfy the above criteria are potentially a CD4/8 cell. Cells that lie too close to the Cy5 or CyFr slopes are labeled as "no-calls". The slopes difference between the CyFr and Cy5 slope are divided into slope regions. Cells that are below the 10% or above the 90% region boundaries are classified as no-calls.

The use of the slope value from the linear regression analysis provides a noise immunity, and improves the robustness of the system. This analysis may be replaced by solving two equations with two unknowns based on the intensity values for channel 0 and channel 1, respectively.

The cross correlation coefficient between corresponding pixels from image 0 and image 1 is determined. If the signal is dominated random noise, one would expect a poor correlation coefficient. A cell with good signal gives a correlation that ranges from 0.9 to 1.0.

The cross-correlation technique can be extended to correlate individual cells with the average cell profile. A composite average cell profile can be generated by averaging the cell profile of all the cells detected. A good correlation coefficient indicates that the cell shape is similar to the average cell shape. An artifact peak usually has a different cell shape profile and thus gives a poorer cross correlation coefficient.

FIG. 10 illustrates an algorithm for computation of the background noise indices, used as described above, with respect to FIG. 9, to define the regions around the line for the two dyes within which a cell will be characterized as containing only that dye.

This background index can be computed for each buffer, or it can be computed across the entire image.

The technique involves defining a plurality of bins for N background baseline noise levels, where N is about 2,000, and each bin 16 bits wide, in one embodiment (block 200). For each buffer, a WXW pixel map surrounding each pixel is defined, such that WXW is large enough to contain almost all the signal from the expected size of the cell. This may be about 5×5 in the present example (block 201).

For each WXW pixel map, the maximum and minimum pixel values are determined for each pixel in images Im1 and Im0 (block 202).

Each pixel is then assigned an integer bin number based on the difference between the maximum and minimum values within the pixel map divided by the size of the allocated bins (block 203). As mentioned above, there may be 2,000 bins, 16 bits wide each for a range of about 32,000 values.

With the integer bin number, the count for the corresponding bin is incremented for that pixel (block 204). After incrementing the bin number, the algorithm determines whether there are more pixels to process for the buffer (block 205). If there are, it loops back to block 201. If not, the algorithm determines the bin number with the highest count (block 206). The background noise index for this buffer is set to the bin number with the highest occurrence times the bin size (block 207). These indices are then stored for both channels (block 208). As mentioned above, the process is carried out for both channels to achieve two separate background noise indices.

FIG. 11 illustrates an algorithm for performing edge detection, as mentioned above. Because the blood sample in this example will contain free dye labelled antibody, a distinct background signal results. This signal is used to locate the boundary of the lumen of the capillary. The average image Im2 from channel 0 and channel 1 is generated (block 300). A specified number N of scans are averaged pixel by pixel to produce an average scan (block 301). The maximum and minimum values are determined from the average scan (block 302). Next, a threshold is set based on the difference between the maximum and the minimum times a factor which ranges from 0.1 to 0.8 (block 303). This establishes a threshold which is a percentage of the average amplitude of fluorescence from a given scan line. The scan lines are then searched from center of the scan to the left until the baseline value is less than the threshold for left edge detection. The left edge is then set as the location where the threshold is crossed (block 304). Similarly, the algorithm searches from the center of the scan to the right until the threshold for right edge detection is passed. The location of the right edge is then defined as the location where the threshold is crossed (block 305). Using edge detection, scanned pixels outside of the detected edges are ignored in the additional processing described above.

Figure 12:
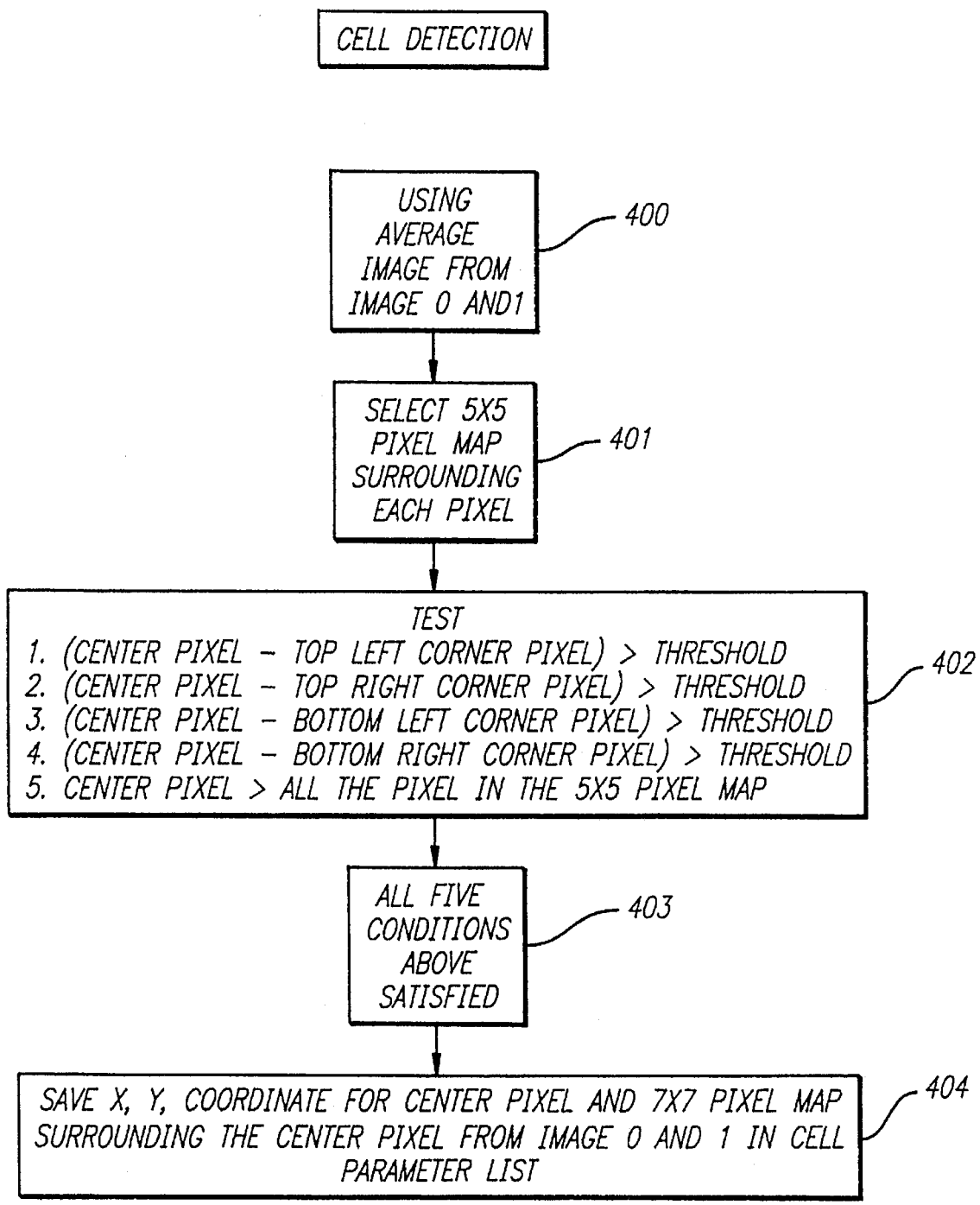
FIG. 12 is a flow chart of the process used for detecting cells according to the present invention.

FIG. 12 illustrates the algorithm for detecting a cell or cell constituent. The cell detection algorithm uses the image Im2, which is based on the average (or sum which for this purpose is substantially the same thing) of images Im0 and Im1 (block 400). A 5×5 pixel map surrounding each pixel is then defined in sequence (block 401). This pixel map is tested. The test is a five step test which involves determining whether the center pixel is the pixel having the highest value of all pixels in the pixel map. If it is, then the test takes the difference between the center pixel and the top left corner pixel and determines whether this difference is greater than a threshold which is assigned for cell or cell constituent detection. Next, the center pixel and the top right corner are used to make the threshold determination. Next, the center pixel and the bottom left corner pixel are used to make the threshold determination. Next, the center pixel and the bottom right corner pixel are used to maker the threshold determination. If the center pixel has the highest value, and another pixel in the map has an equal value, then the algorithm passes the test. In order to avoid counting a cell twice, in this instance, the center pixel value is incremented by one, so that when the other pixel value having the high value is encountered, it will be determined that it is not the highest value pixel (block 402).

If all five conditions have been satisfied (block 403), the x and y coordinate for the center pixel is saved, and a 7×7 pixel map, or neighborhood, surrounding the center pixel is saved from each image Im0 and Im1 in the cell parameter list (block 404). These values can be used for later processing of the data as described above.

Using the averaged (or summed) image for cell detection provides better cell resolution, because of magnitude of the signal from any one of the two dyes may be very low on a given cell. This cell or cell constituent detection is based on the maximum and minimum values in the neighborhood around the detected cell, rather than an absolute peak value. This provides immunity from variance in background levels over the scanned region.

Figure 13:
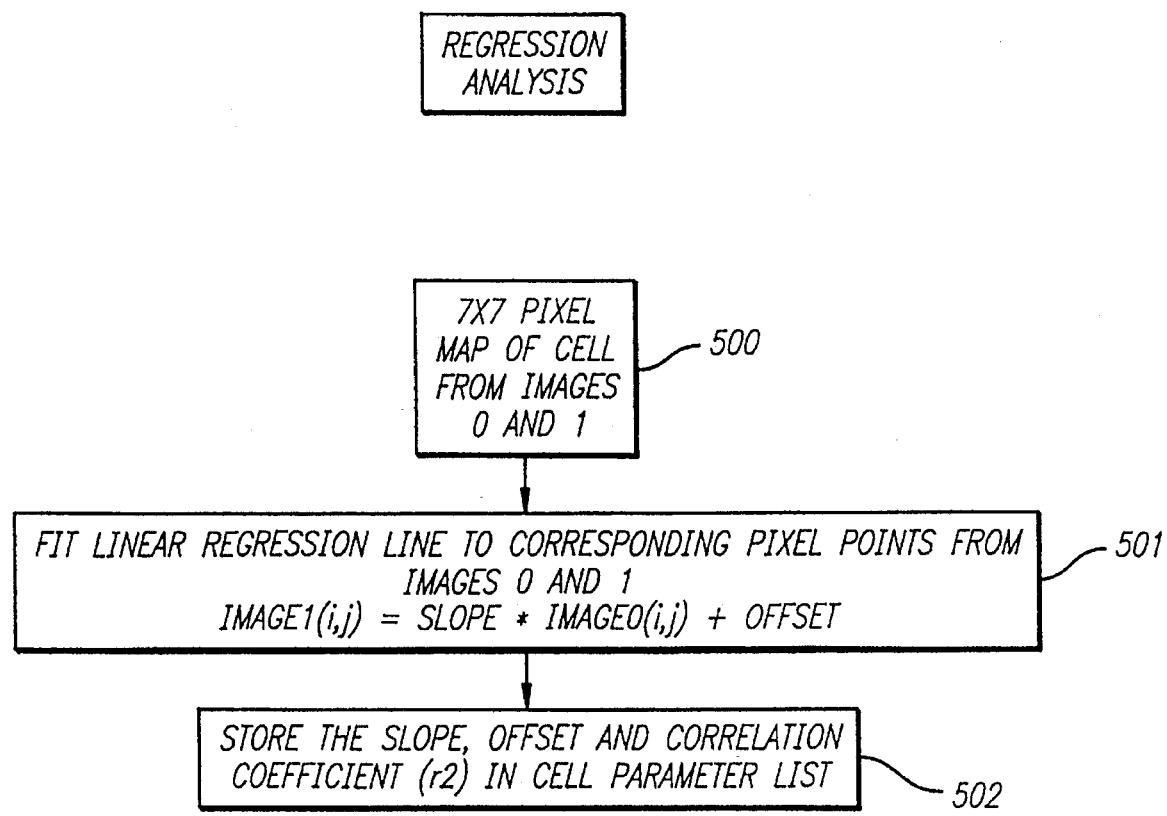
FIG. 13 is a flow chart illustrating the process for linear regression analysis according to the present invention.

FIG. 13 illustrates the basic algorithm for linear regression analysis of the 7×7 pixel map. The linear regression analysis begins by taking the 7×7 pixel map of a detected cell from both images I0 and I1 (block 500). A linear regression line is fitted for corresponding pixel points from images Im0 and Im1 over the indices for the row i and the column j, such that Im1 (i,j) approximates to the slope times Im0 (i,j) plus an offset (block 501). After fitting the regression line, the slope, offset and correlation coefficient r2 (goodness of fit) are stored in the cell parameter list (block 502).

Thus, a linear regression line fit is computed between the corresponding pixels from image 0 and image 1 and the slope and goodness of fit values are obtained. The slope determined indicates whether the cell is stained with 1 of 2 antibodies. Using a 7×7 pixel map to determine the slope gives a better estimate of the characteristics of the cell. The goodness of fit indicates the goodness of the data. The advantages of the linear regression analysis include noise reduction, a good estimate of signal quality, a system insensitive to baseline subtraction, and the well defined orthogonal coordinates.

In sum, a method and apparatus is provided for processing data generated by one or more channels of data, where the channels include information relevant to more than one characteristic to be determined, and are taken from a container. The technique allows for counting and characterizing the cells or cell constituents within the contained region with minimum operator handling of the samples, repeatability, and efficient utilization of processing resources.

The data processing resources accomplish data collection, image averaging for capillary edge and cell detection operations, background noise determination, baseline removal, and cell characterization.

The data from a detected cell or cell constituent is then extracted by saving it into a cell parameter list in memory. This allows continuous scans of large volumes of data, with processing of the data saved for later steps when more processing resources may be available. Also, it allows reanalysis of data for detected cells in the future based on much reduced file sizes, as compared to what would result if the entire 200 by 10,000 pixel file must be saved for later analysis.

The present invention provides a system for processing scanned data which is very robust and accurate. It allows concurrent data collection and analysis, as well as analysis of data after collection. Further, it allows for completion of data analysis very rapidly, shortly after completion of the data collection systems.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

---

APPENDIX A
Copyright Biometric Imaging, Inc., 1994
SOURCE CODE FOR CELL CHARACTERIZATION

---

```
const float kCellCorrelationCoefThreshold = 0.8;
CELL-TYPE CCell::CellClassification()
{
    float   maxSlope = CyFrSlope -
            ((CyFrSlope-CySSlope) * 0.1);
    float   minSlope = Cy5Slope +
            ((CyFrSlope-Cy5Slope) * 0.1);
    if ( (cellCorrelationCoef <
    kCellCorrelationCoefThreshold) ||
            (peakValue0 < noiseThreshold0) ||
            (peakValue1 < noisethreshold1) )
            return (NON_CELL);       // noise peak
    else if ( (peakValue1 > (CyFrSlope * peakValue0 +
    noiseLevel) )
            return (CYFR_POSITIVE);   //monocyte or NK cells
    else if (peakValue1 < (Cy5Slope * peakValue0 +
    noiseLevel) )
            return(CYS_POSITIVE);    //CD3 cells
    else if ( (cellSlope > maxSlope) || (cellSlope < minSlope) )
            return (NO_CALL);        //No call
    else
            return (CYFR_CYF_POSITIVE);// CD4/8 cell
    }
```

---

What is claimed is:

1. A method for analyzing a sample containing cells to detect and characterize target cells having first detectable characteristics and second detectable characteristics in a fixed volume capillary that contains a fluorescent background which exhibits background characteristics, the method comprising:

scanning the fixed volume capillary containing the sample to generate a first channel of data and a second channel of data, wherein the first channel of data includes the first detectable characteristics and first background characteristics and the second channel of data includes the second detectable characteristics and second background characteristics;

sampling the first and the second channels of data to produce corresponding first and second sets of pixel values;

loading the first and the second sets of pixel values into a pixel map buffer;

analyzing the first and the second sets of pixel values in the pixel map buffer to identify a peak event indicative of the target cell;

saving a first neighborhood of pixel values from the first set of pixel values and a second neighborhood of pixel values from the second set of pixel values for the peak event;

performing linear regression to correct for detection of the second detectable characteristics in the first channel and for detection of the first detectable characteristics in the second channel;

filtering the first neighborhood of pixel values and the second neighborhood of pixel values for the peak event using predetermined peak characteristic so as to adjust for the first and the second background characteristics;

generating a first intensity value from the first neighborhood and a second intensity value from the second neighborhood for the peak event; and comparing the first intensity value and the second intensity value for the peak event to a first threshold to classify the target cell.

2. The method of claim 1, further comprising processing the first and the second sets of pixel values to calculate a background index, wherein the step of analyzing the first and the second sets of pixel values includes identifying the peak event which exceeds a second threshold and wherein the first threshold and the second threshold are determined as a function of the background index.

3. The method of claim 1, wherein the capillary has edges and at least one channel of data has information relevant to the edges of the capillary, the method further comprising processing at least one set of pixel values corresponding to at least one channel of data to detect the edges of the capillary, and wherein the step of analyzing the first and the second sets of pixel values in the pixel map buffer includes ignoring pixels outside the edges of the capillary.

4. The method of claim 1, wherein the target cells are blood cells.

5. The method of claim 1, wherein the target cells are leukocytes and the sample contains red blood cells.

6. The method of claim 1, wherein the target cells are labeled with a fluorophore excitable in a range of 600 to 1,000 nanometers.

7. A method for analyzing a sample of cells in a capillary that contains fluorescent matter which exhibits background characteristics so as to identify and classify a plurality of subsets of cells having detectable characteristics, the method comprising:

scanning the capillary containing the sample to generate two channels of data, each channel of data containing information relevant to two detectable characteristics and to the background characteristics;

sampling the two channels of data to produce two sets of pixel values representing information relevant to the two detectable characteristics and to the background characteristics;

loading the two sets of pixel values into a pixel map buffer;

analyzing the two sets of pixel values to identify a peak event;

saving two neighborhoods of pixel values corresponding to the peak event;

performing linear regression on the two neighborhoods of pixel values to discriminate the two detectable characteristics in the two channels for the peak event;

filtering the two neighborhoods of pixel values using predetermined characteristics of the peak event so as to adjust for the background characteristics;

generating two intensity values for the peak event; and classifying the peak event as one of a plurality of subsets of cells by comparing the two intensity values to a first threshold.

8. The method of claim 7, further comprising processing the two sets of pixel values to calculate a background index, wherein the step of analyzing the two sets of pixel values includes identifying the peak event which exceeds a second threshold, and wherein the first threshold and the second threshold are determined as a function of the background index.

9. An apparatus for analysis of a sample containing cells to detect and characterize target cells having detectable characteristics in a fluorescent background that has background characteristics, the apparatus comprising:

a scanner which scans the sample to generate two channels of data, each channel containing information relevant to two detectable characteristics and the background characteristics;

means for sampling the two channels of data to generate two streams of pixel values;

a processing system having memory, said processing system being coupled to said means for sampling and having first resources which load the two streams of pixel values into a pixel map buffer, which analyze the two streams of pixel values to identify a peak event indicative of the target cell and which save two neighborhoods of pixel values for the peak event; and second resources which classify the peak event based upon the two neighborhoods of pixel values, said second resources configured to perform linear regression between the two neighborhoods of pixel values to discriminate the two detectable characteristics in the two channels, to filter the two neighborhoods of pixel values using predetermined characteristics of peak events so as to adjust for the background characteristics, to generate two intensity values corresponding to the two neighborhoods, and to classify the target cell by applying the two intensity values to a first threshold.

10. The apparatus of claim 9, wherein said second resources are furthered configured to detect an edge of the sample and ignore pixel values outside the detected edge.

11. The apparatus of claim 9, wherein said second resources are further configured to generate two intensity values for the target cell independent of neighborhoods related to other peak events.

12. The apparatus of claim 9, wherein said processing system is further configured to process the two streams of pixel values to calculate a background index and to identify the peak event using a second threshold, wherein the first threshold and the second threshold are determined as a function of the background index.

13. The apparatus of claim 9, wherein the sample contains blood cells.

14. The apparatus of claim 9, wherein the target cells are leukocytes and the sample contains red blood cells.

15. The apparatus of claim 9, wherein the target cells are labeled with a fluorophore excitable in a range of 600 to 1,000 nanometers.

* * * * *